US012558115B2

(12) United States Patent
Byrne et al.

(10) Patent No.: US 12,558,115 B2
(45) Date of Patent: Feb. 24, 2026

(54) MECHANISM FOR DICING CARTILAGE

(71) Applicant: The Johns Hopkins University, Baltimore, MD (US)

(72) Inventors: Patrick J. Byrne, Baltimore, MD (US); Brooke Stephanian, Terre Haute, IN (US); Sabin Karki, Zionsville, IN (US); Paarth Sharma, Mentone, CA (US); Kirby Tso Leo, Baltimore, MD (US); Marc Anthony Di Meo, Windsor (CA); Mitsuki Ota, Honolulu, HI (US); Millan Patel, Macungie, PA (US); Thomas Benassi, Towson, MD (US); Nicholas James Durr, Baltimore, MD (US); Allison Rosen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 555 days.

(21) Appl. No.: 17/905,449

(22) PCT Filed: Mar. 8, 2021

(86) PCT No.: PCT/US2021/021354
§ 371 (c)(1),
(2) Date: Sep. 1, 2022

(87) PCT Pub. No.: WO2021/178955
PCT Pub. Date: Sep. 10, 2021

(65) Prior Publication Data
US 2023/0181209 A1 Jun. 15, 2023

Related U.S. Application Data

(60) Provisional application No. 62/985,932, filed on Mar. 6, 2020.

(51) Int. Cl.
A61B 17/32 (2006.01)
A61B 17/00 (2006.01)
A61B 17/322 (2006.01)

(52) U.S. Cl.
CPC .... A61B 17/32 (2013.01); A61B 2017/00792 (2013.01); A61B 2017/3225 (2013.01)

(58) Field of Classification Search
CPC ......... A60B 2017/320008; A61B 2017/00792; A61B 17/32–326; A61B 2017/320004–3225
(Continued)

(56) References Cited

U.S. PATENT DOCUMENTS 3,815,605 A 6/1974 Schmidt et al.
4,773,415 A * 9/1988 Tan ..................... A61F 9/00736
600/209

(Continued)

FOREIGN PATENT DOCUMENTS

AU 20133312723 B2 3/2014

OTHER PUBLICATIONS

International Search Report and Written Opinion issued in Application No. PCT/US2021/021354; Dated Jun. 10, 2021, 6 Pages.

*Primary Examiner* — Matthew J Lawson
(74) *Attorney, Agent, or Firm* — Harrity & Harrity, LLP

(57) ABSTRACT

A cartilage dicing device according to an embodiment of the present invention includes blades disposed in a housing configured to mitigate entry of the cartilage into the housing of the device. The device includes a number of circular blades used to dice the cartilage in a uniform fashion. The blades are disposed in a housing with a base that prevents the tissue from entering the body of the housing, which ensures
(Continued)

that more of the tissue is available to be diced and used in a medical procedure. The blades are spaced at uniform distance.

20 Claims, 37 Drawing Sheets

(58) Field of Classification Search
 USPC ......................................................... 606/114
 See application file for complete search history.

(56) References Cited

U.S. PATENT DOCUMENTS

| | | | | |
|---|---|---|---|---|
| 6,248,114 | B1 * | 6/2001 | Ysebaert | A61B 17/322 606/132 |
| 8,100,823 | B2 | 1/2012 | Harp | |
| 11,331,109 | B2 * | 5/2022 | Lee | A61B 17/1635 |
| 2004/0172045 | A1 * | 9/2004 | Eriksson | A61B 17/322 606/132 |
| 2004/0175690 | A1 * | 9/2004 | Mishra | A61B 17/322 435/379 |
| 2004/0230215 | A1 * | 11/2004 | Eriksson | A61B 17/322 606/180 |
| 2011/0098628 | A1 | 4/2011 | Yeung et al. | |
| 2011/0247220 | A1 * | 10/2011 | Whited | A61B 17/322 30/276 |
| 2014/0107668 | A1 * | 4/2014 | Zolotov | A61B 17/322 606/132 |
| 2017/0303955 | A1 | 10/2017 | Yokoyama | |
| 2019/0090897 | A1 * | 3/2019 | Ma | A61B 17/32053 |
| 2020/0086001 | A1 * | 3/2020 | Maccagnan | A61L 27/3687 |
| 2020/0121328 | A1 * | 4/2020 | Lee | A61B 17/1637 |
| 2021/0323045 | A1 * | 10/2021 | Lujan | B26B 5/006 |
| 2023/0146318 | A1 * | 5/2023 | Sjöberg | A61B 17/32093 606/132 |

* cited by examiner

54
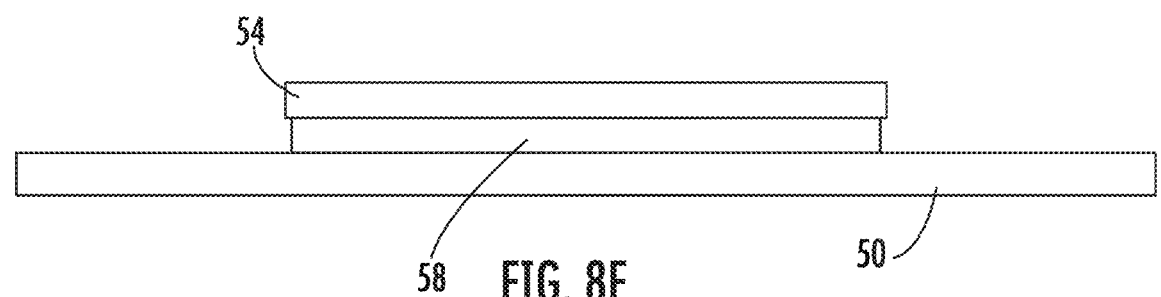
58    FIG. 8F                50

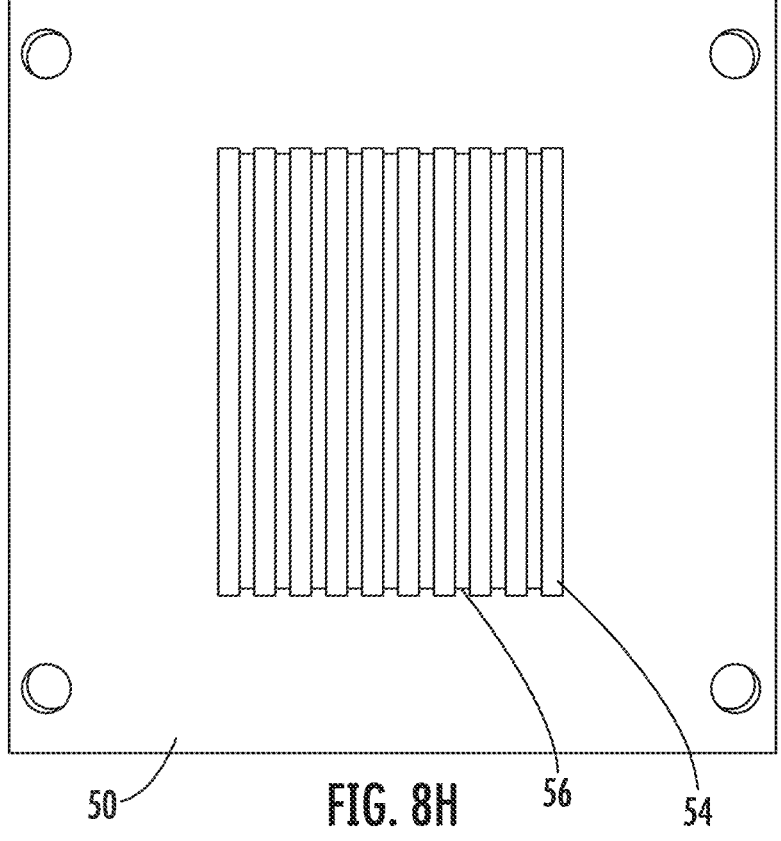
50    FIG. 8H      56      54

64

66

68

60

26    27

26

MECHANISM FOR DICING CARTILAGE

CROSS REFERENCE TO RELATED APPLICATIONS

This application is a 371 national stage of PCT Application No. PCT/US2021/021354 filed on Mar. 8, 2021, entitled "MECHANISM FOR DICING CARTILAGE", which claims the benefit of U.S. Provisional Patent Application No. 62/985,932 filed on Mar. 6, 2020, which are incorporated by reference, herein, in their entirety.

FIELD OF THE INVENTION

The present invention relates generally to medical devices. More particularly, the present invention relates to a device for dicing cartilage and preventing entry of tissue into the cutting apparatus.

BACKGROUND OF THE INVENTION

Rhinoplasties are surgical procedures in which plastic surgeons augment or reduce structures of the nose to resolve functional and aesthetic issues. Over 200,000 rhinoplasties are performed in the US annually, and a significant percentage of these procedures require the use of cartilage grafts, which are pieces of cartilage harvested from the patient's septum, rib, ear, or cadaveric tissue. Prior to implantation, grafts are shaped into the desired form by the surgeon by either carving, crushing, shaving, or dicing and molding of the tissue.

While carving is the most common method of cartilage shaping, dicing has been shown in literature to be the optimal clinical technique because it results in the fewest postoperative surgical complications (warping, resorption, or cell death) when compared to carving, crushing, or shaving. Revision rates using the dicing technique are estimated to be much lower than the overall procedure revision rate for all rhinoplasties.

However, surgical adoption of the dicing technique has been limited due to the labor-intensive and time-consuming process of manually dicing cartilage pieces with a scalpel to the desired size (1 mm pieces). Surgeon feedback and literature has demonstrated that the effort of manually dicing represents a major pain point, as the process requires the surgeon's complete attention and can add up to two hours to procedure time, depending on the volume of cartilage needed. The time required to dice cartilage is the primary factor discouraging surgeon use of dicing techniques, as reported in literature and surgeon feedback. The shape of harvested cartilage differs between patients depending on the amount and location of usable tissue, further challenging the creation of uniformly diced pieces. Additionally, uneven dice sizes in grafts can contribute to postoperative complications such as graft visibility, breakage, or migration.

Therefore, it would be advantageous to provide a device for dicing cartilage and preventing entry of tissue into the cutting apparatus so that plastic surgeons can quickly produce consistent diced cartilage grafts for rhinoplasty procedures, thereby increasing adoption of diced cartilage methods and reducing revision rates.

SUMMARY OF THE INVENTION

The foregoing needs are met, to a great extent, by the present invention, wherein in one aspect a device assembly includes a housing and a blade assembly wherein the blade assembly is configured to cut tissue. The device also includes a blade base, wherein the blade base is configured to scrape tissue from the blade assembly.

In accordance with an aspect of the present invention, the blade assembly has nine blades. The nine blades take the form of circular blades. The blades are configured to rotate about an axis. The blade base includes nine slits to accommodate the nine blades. The blade base can include O-rings and anchors to hold the O-rings in place, such that the O-rings scrape tissue from the blade assembly. The anchors can take the form of hooks or columns. The blade base can also include a removable portion to further scrape tissue from the blade assembly. The housing is further configured to protect a hand of the user from the blade assembly.

In accordance with another aspect of the present invention, a device assembly includes a housing. The device includes a blade assembly. The blade assembly is configured to cut tissue. The device also includes a blade base. The blade base is configured to scrape tissue from the blade assembly. The blade base defines an opening configured to accommodate the blade assembly. The blade base comprises material surrounding the opening, wherein the material surrounding the opening is configured to further remove tissue from the blades.

In accordance with yet another aspect of the present invention, the blade assembly takes the form of a blade. The blade takes the form of a circular blade, and the blade is configured to rotate about an axis. The blade assembly further can include a number of blades. The material surrounding the openings of the blade base takes the form of O-rings, such that the O-rings scrape tissue from the blade assembly. The blade base includes a removable portion to further scrape tissue from the blade assembly. The housing is configured to protect a hand of the user from the blade assembly. The blade assembly is retractable into the housing.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 6A-6G illustrate views of a blade base, according to an embodiment of the present invention.

FIGS. 8A-8H illustrate views of a columnar O-ring base, according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

A cartilage dicing device according to an embodiment of the present invention includes blades disposed in a housing configured to mitigate entry of the cartilage into the housing of the device. The device includes a number of circular blades used to dice the cartilage in a uniform fashion. The blades are disposed in a housing with a base that prevents the tissue from entering the body of the housing, which ensures that more of the tissue is available to be diced and used in a medical procedure. The blades are spaced at uniform distance.

Figure 1:
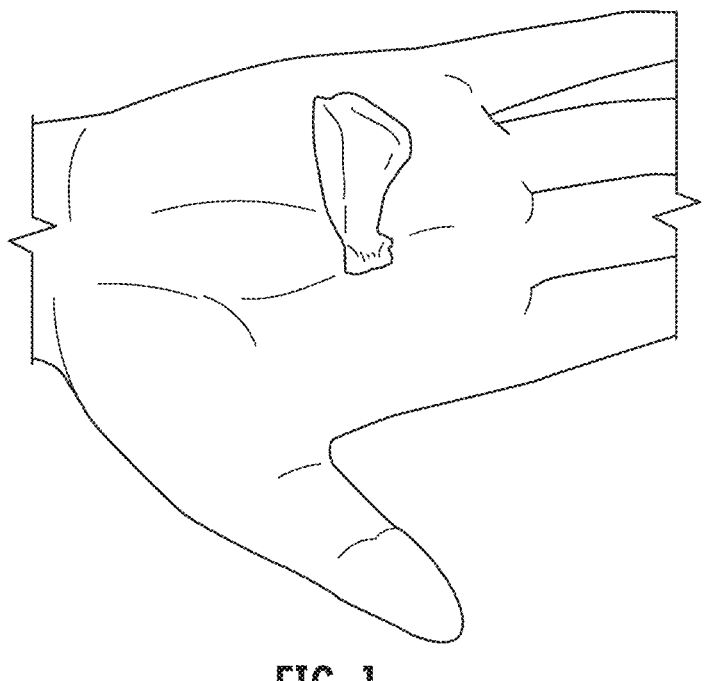
FIG. 1 illustrates a piece of cartilage to be diced, according to an embodiment of the present invention.
Figure 2:
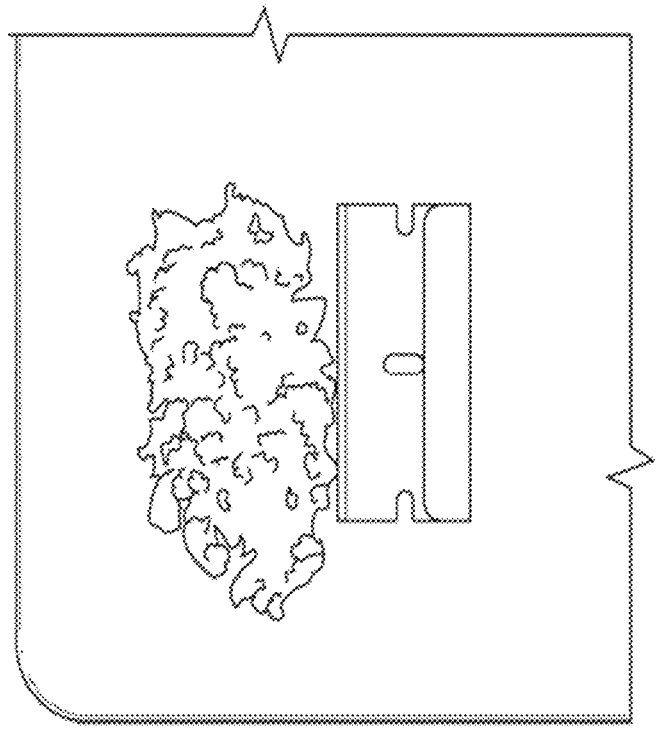
FIG. 2 illustrates uniformly diced cartilage, according to an embodiment of the present invention.

FIG. 1 illustrates a piece of cartilage to be diced, and FIG. 2 illustrates diced cartilage, according to an embodiment of the present invention. The cartilage can be taken from the ear, septum, or rib of the patient or a donor. Because a separate procedure is often required to harvest patient cartilage and/or additional donor cartilage may not be available in the operating room, it is essential to maximize the usability of the cartilage. Therefore, physicians often avoid dicing, as it is time consuming to prepare the cartilage in a way that also preserves the highest amount of useable tissue. Diced cartilage, as illustrated in FIG. 2, yields high quality surgical results.

Figure 3A:
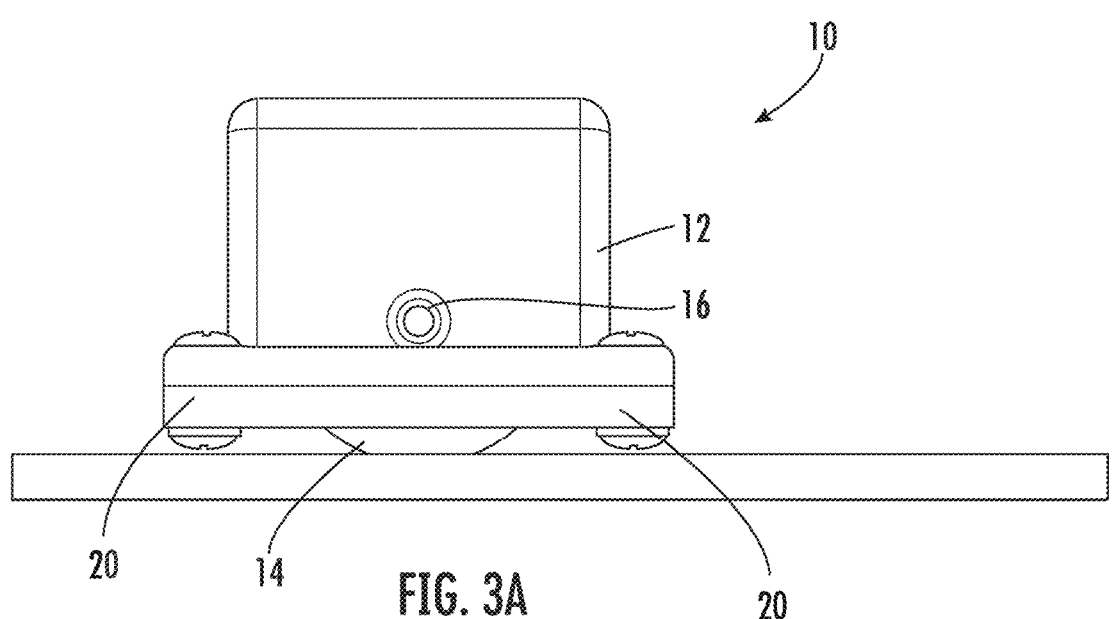
FIGS. 3A-3C illustrate side views of a cartilage dicing device, according to an embodiment of the present invention.
Figure 3B:
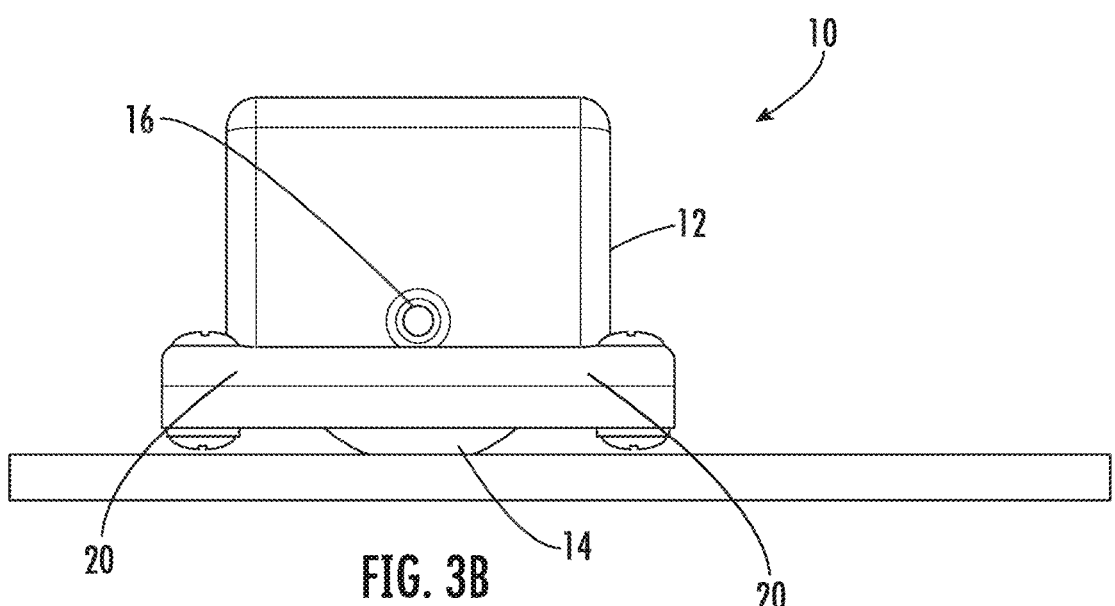
Figure 3C:
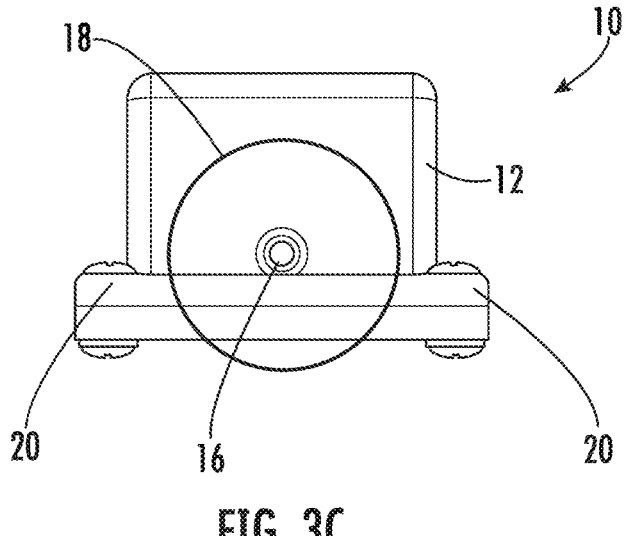

FIGS. 3A-3C illustrate side views of a cartilage dicing device, according to an embodiment of the present invention. The cartilage dicing device 10 of the present invention includes a housing 12 and blade assembly 14. The blade assembly 14 rotates about axle 16. The axle 16 and the blade assembly 14 are configured such that the blades of the assembly 14 rotate linearly over the tissue to be diced. The blade assembly 14 can rotate either forward or backward about the axle 16. The housing 12 is configured to receive the full diameter 18 of the blade assembly 14 and allow the blade assembly 14 to rotate freely about the axle 16. The housing 12 can also include flanges 20 to prop up the device 10 when it is not in use. In other embodiments of the device, these flanges may be eliminated without affecting the functionality of the device 10. The housing 12 can be formed from a plastic, metal, or other material known to or conceivable to one of skill in the art. In some embodiments, the blade assembly 14 can be removable from the housing 12. In such embodiments, the housing 12 can be formed from a material that can be sanitized by a method such as autoclaving. In such embodiments, portions of the device 10 may be replaceable, such as the blade assembly 14. FIG. 3A shows an exemplary axle diameter of 6.65 mm. FIG. 3B shows an exemplary base length of 80 mm, and FIG. 3C illustrates an exemplary blade diameter of 45 mm. The device can be formed from materials that are compatible with high-heat cleaning, such as autoclaving, or other sanitization methods, such that the device can be reusable. In other embodiments, the housing 12 can be formed together with the blade assembly 14. In such embodiments the blade assembly 14 can be formed integrally with the housing 12 and is not removable.

In some embodiments the blades are rotated about the axle by rolling the device forward and backward on a surface. In some embodiments, the device can include an electrically powered mechanism or motor to move the blades about the axle. A device according to such an embodiment can include a button or a switch for engaging the motor and the rotation of the blades. Alternately, the device can include a manual mechanism for turning the blades. Such a manual mechanism could take the form of a crankshaft, push button, lever, or any other suitable mechanism known to or conceivable to one of skill in the art. In other embodiments, the device may be fully automated, such that tissue is introduced into an automated device and then diced. A device according to an embodiment of the present invention can also include a spring-based timer to lock blades for auto-timed cutting capabilities.

Figure 4:
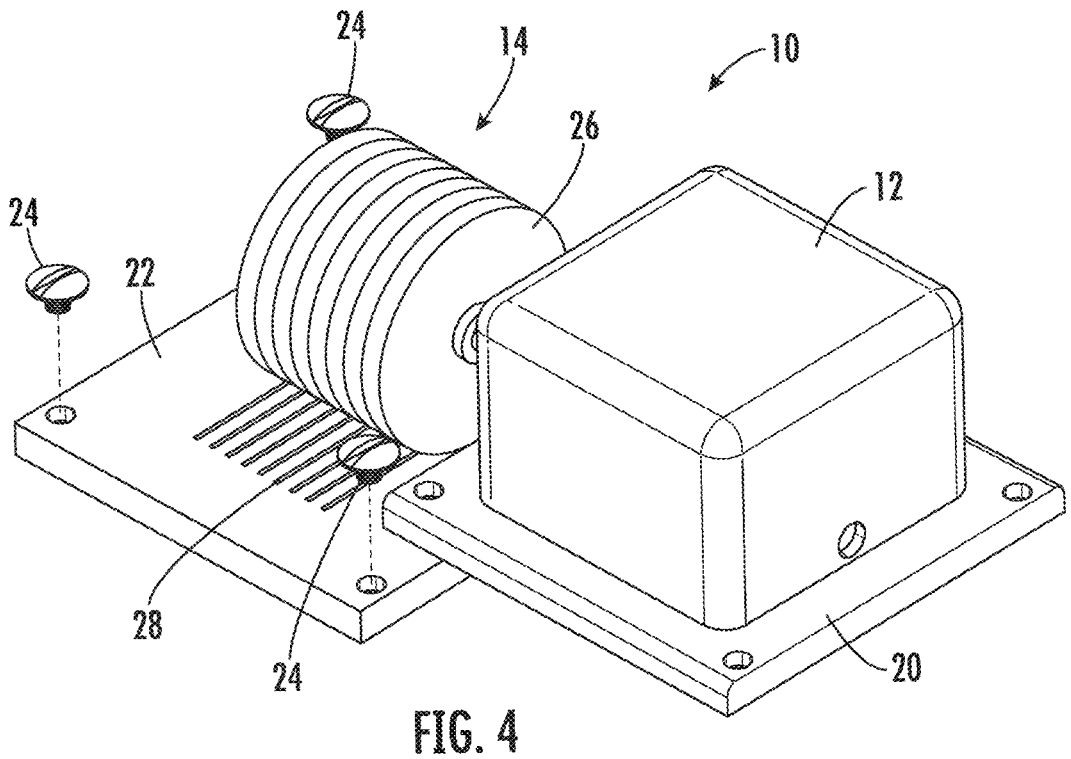
FIG. 4 illustrates an exploded view of a cartilage dicing device, according to an embodiment of the present invention.

FIG. 4 illustrates an exploded view of a cartilage dicing device, according to an embodiment of the present invention. The device 10, as illustrated in FIG. 4, includes the housing 12, blade assembly 14, axle 16, and base 22. Screws 24 connect the base 22 to the housing 12. The blade assembly 14 includes a number of blades 26. Nine blades 26 are illustrated in FIG. 4. This number of blades 26 is not to be considered limiting, and any number of blades 26 deemed suitable to one of skill in the art could be used. The base 22 is configured to scrape tissue from the blades 26, as they rotate through the housing 12. As illustrated in FIG. 4, the base 22 includes a number of slits 28, wherein each blade 26 rotates within its own slit 28. A number of different embodiments of the base 22 configured to scrape the blades 26 will be described further herein. As described above, the housing can be formed from a plastic, metal, or other material known to or conceivable to one of skill in the art. The blades 26 can be formed from a metal, composite, or other material known to or conceivable to one of skill in the art. A device according to an embodiment of the present invention can also be modular. A modular embodiment could include a detachable housing, handle, removable and replaceable blade assembly and blades, or cartilage removal mechanism. A modular embodiment could include all removable elements or can have only one or a couple of removable elements, as is known to or conceivable to one of skill in the art. While the base 22 is shown in FIG. 4 as being attached with screws 24, it is to be understood that any means or method for attaching the base 22 to the housing 12 known to or conceivable to one of skill in the art could also be used.

It is also possible, as would be known to one of skill in the art, that the base 22 can be formed integrally with the housing 12, such that the base 22 and housing 12 are one piece.

FIGS. 5A-5D illustrate views of a housing of a cartilage dicing device, according to an embodiment of the present invention. As illustrated in FIGS. 5A-5D, the housing 12 is configured to accommodate the rotation of the blades about the axle. The housing 12 as illustrated is generally square in shape and includes a flange 20. However, any suitable shape known to or conceivable to one of skill in the art could also be used. In addition, the housing 12 can include grips, texturized sides, and other features. The housing may attach to the blade base by a lock-fit assembly or any other mechanism known to or conceivable by one of skill in the art. The housing is configured to protect a hand of the user from the blade assembly. The housing 12 can be formed from a variety of materials including metal, plastic, composites or any other material known to or conceivable to one of skill in the art. It is also possible that in some configurations the housing 12 is made from a material that can be sanitized via autoclave or other method known to or conceivable to one of skill in the art.

Figure 5A:
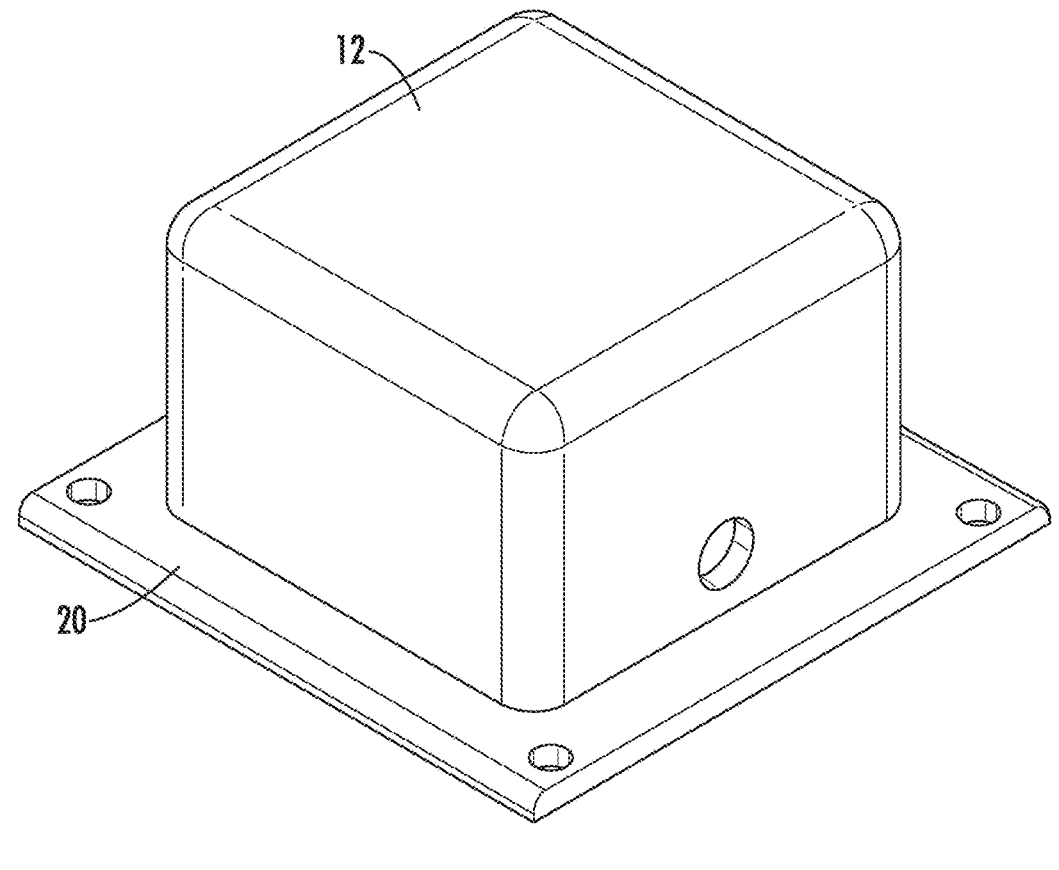
FIGS. 5A-5D illustrate views of a housing of a cartilage dicing device, according to an embodiment of the present invention.
Figure 5B:
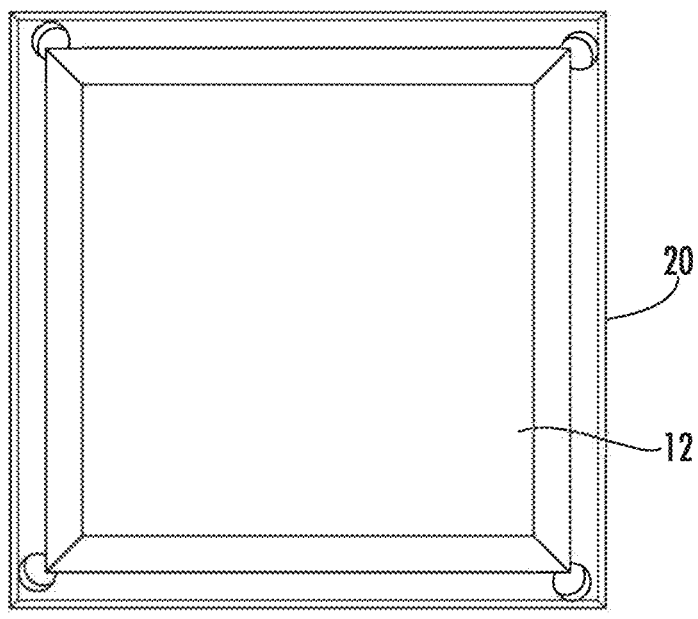
Figure 5C:
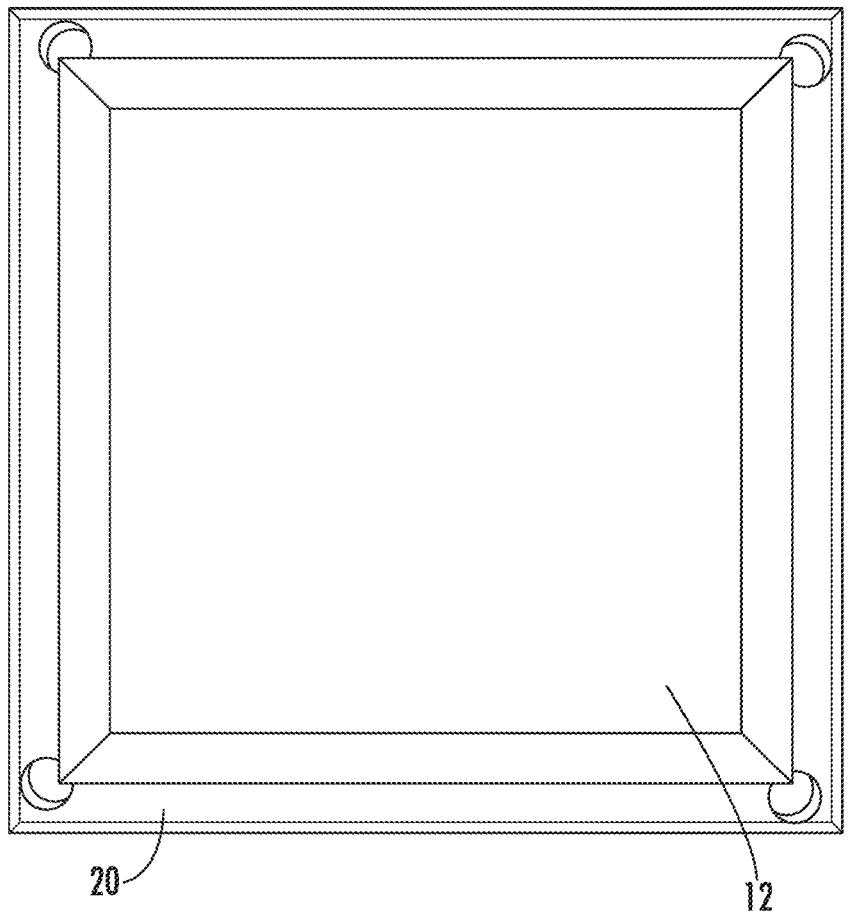
Figure 5D:
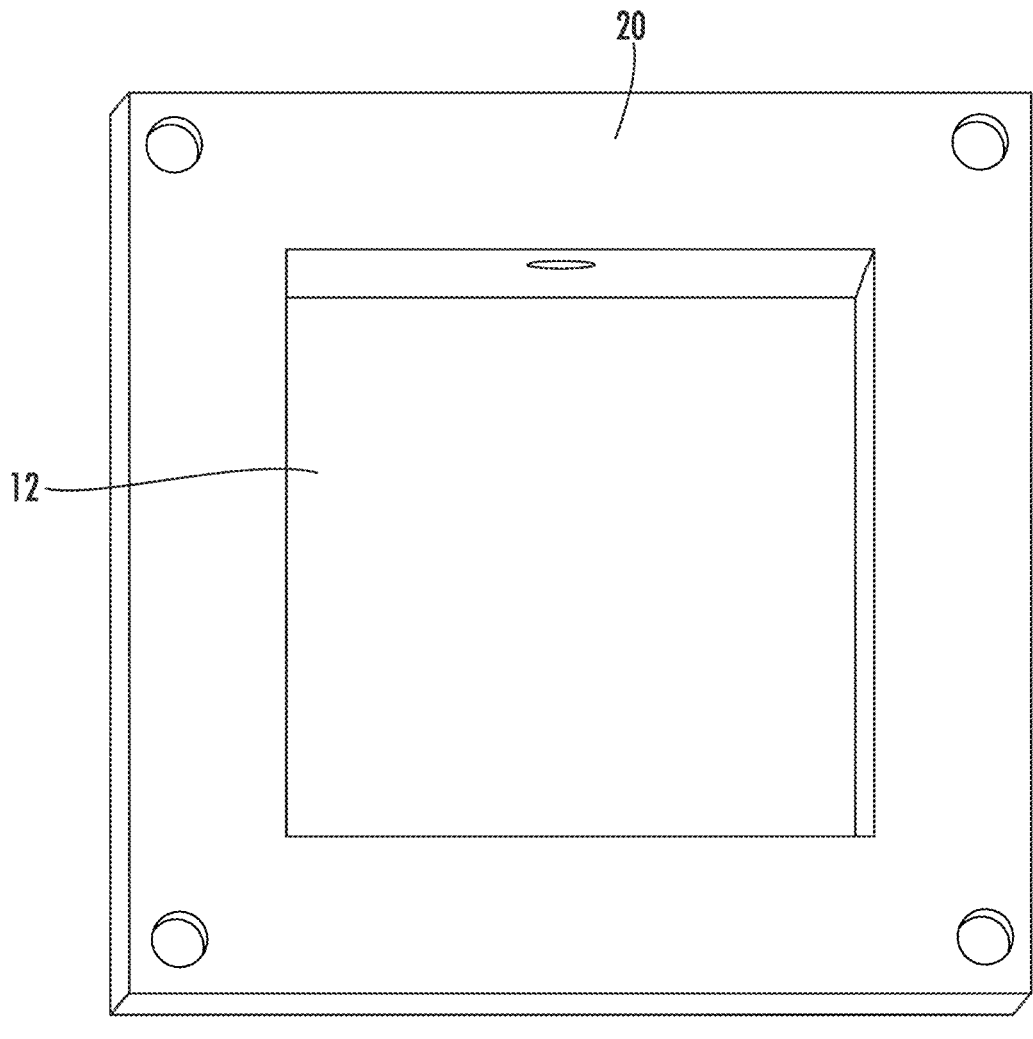

FIG. 5B illustrates an exemplary screw hole diameter of 5.08 mm. FIG. 5C illustrates an exemplary housing length of 54 mm, and FIG. 5D illustrates an exemplary flange length of 80 mm. These measurements are included only by way of example and are not meant to be considered limiting. Any suitable sizing and dimensions for the device known to or conceivable to one of skill in the art can be used. It is also possible to manufacture the device in different sizes for physicians with different hand sizes, preferences, and surgical applications. In some embodiments, the housing can be extended such that there is no exposure of the blades to the environment. The housing can also include a mechanism for collecting tissue within the device. In other embodiments the housing can contain a heat source for warming tissue before it is diced. This allows for easier dicing of the tissue. In other embodiments, the housing may include a mold or other feature used to collect the tissue together after processing, such that cartilage can be washed out into the mold to form a graft or to store the diced tissue. Additionally, the housing or other part of the device can include an indicator to give a qualitative/quantitative estimate of cartilage size.

Figure 6A:
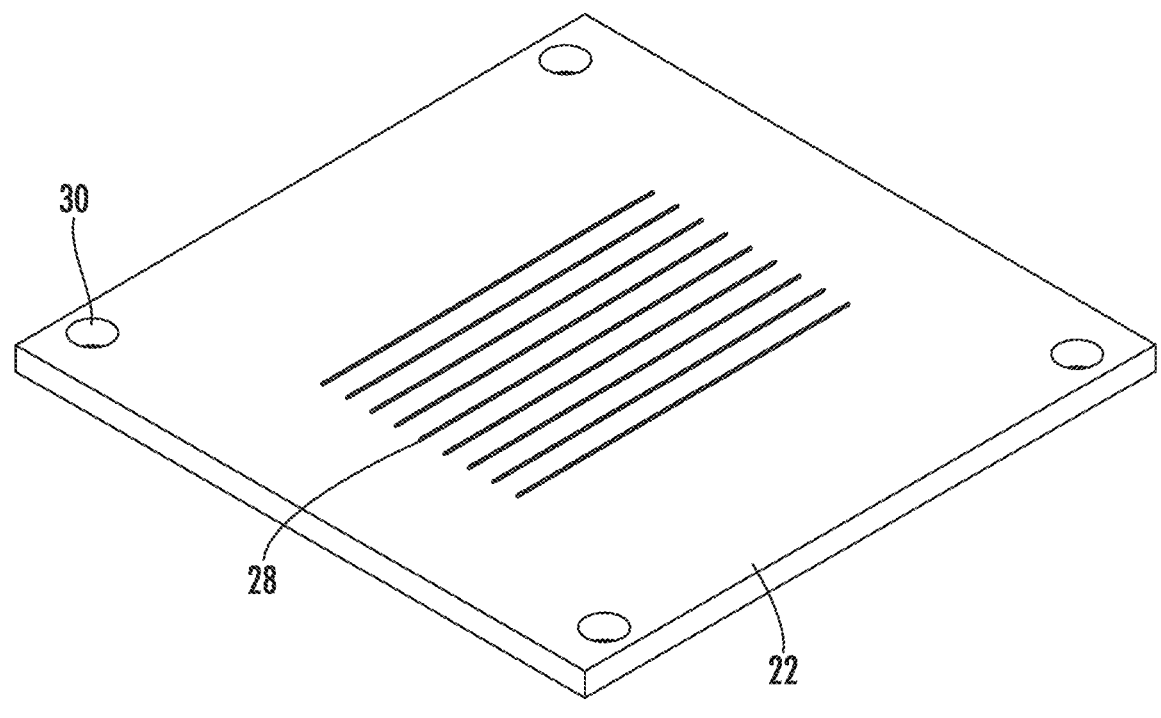
Figure 6B:
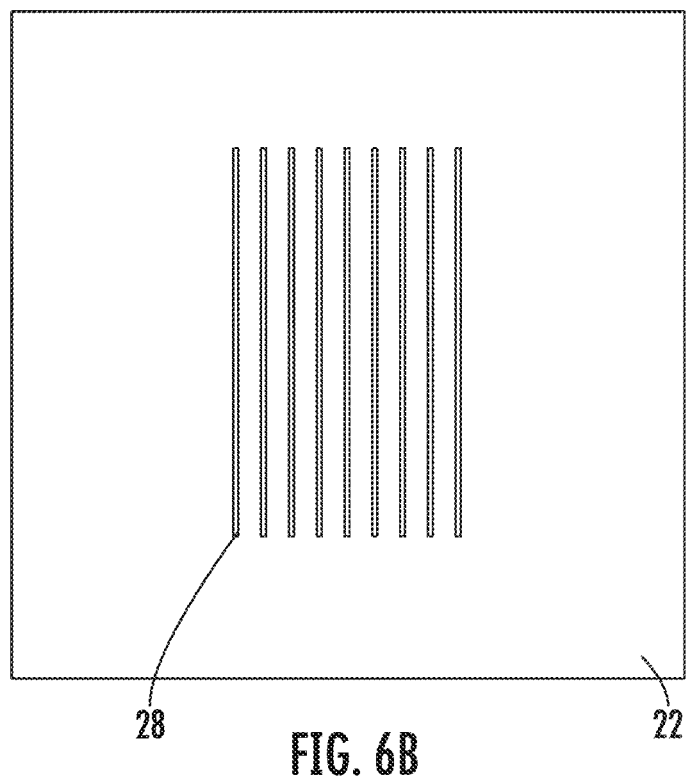
Figure 6C:
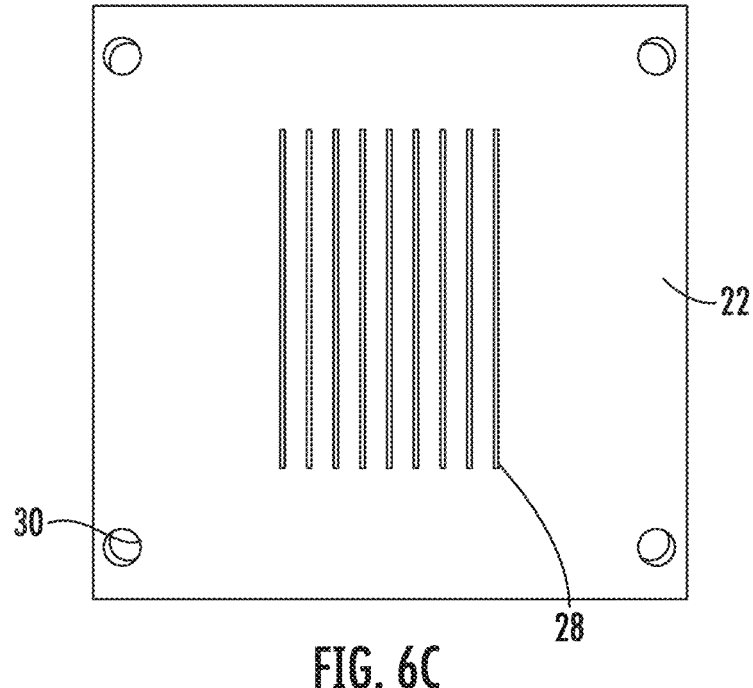
Figure 6D:
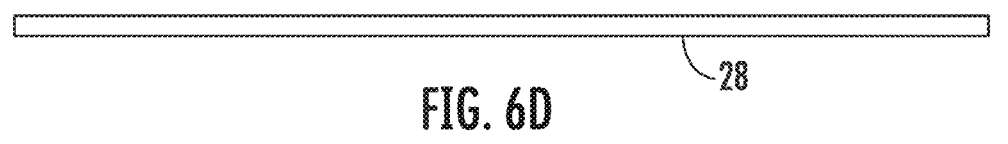
Figure 6E:
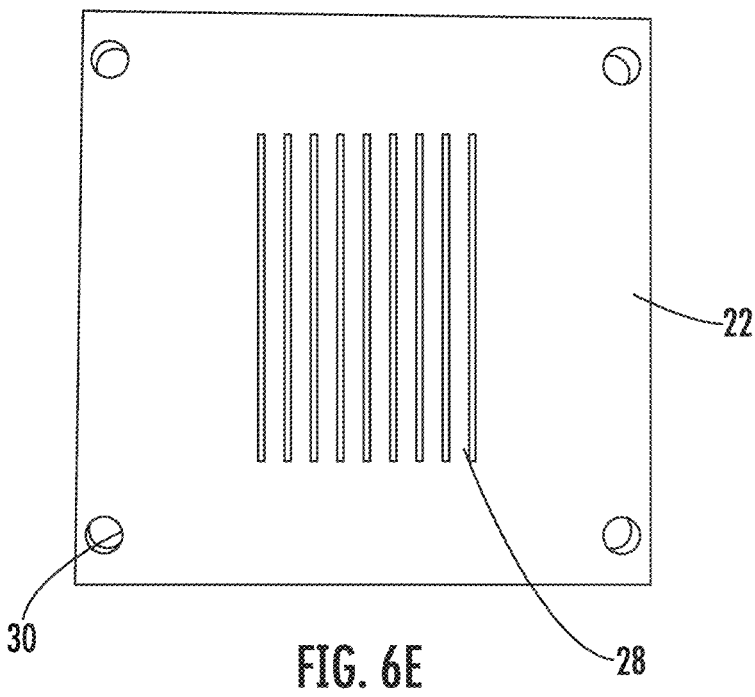
Figure 6F:
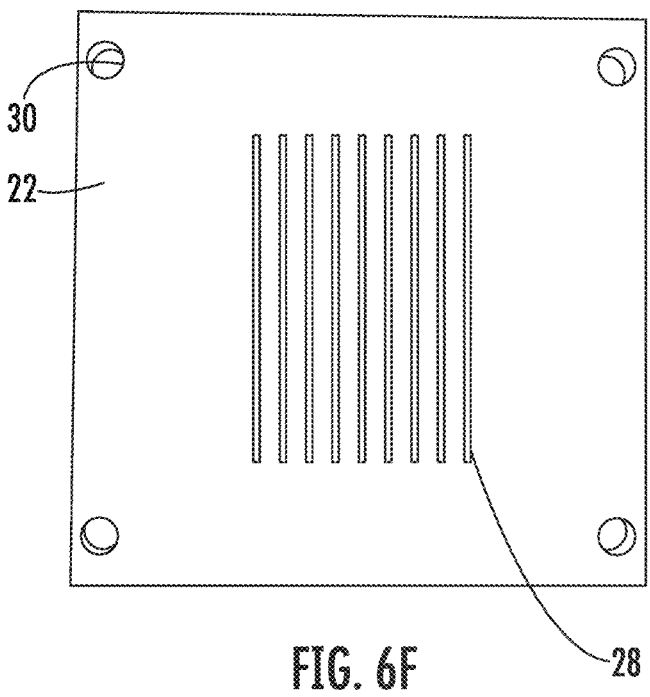
Figure 6G:
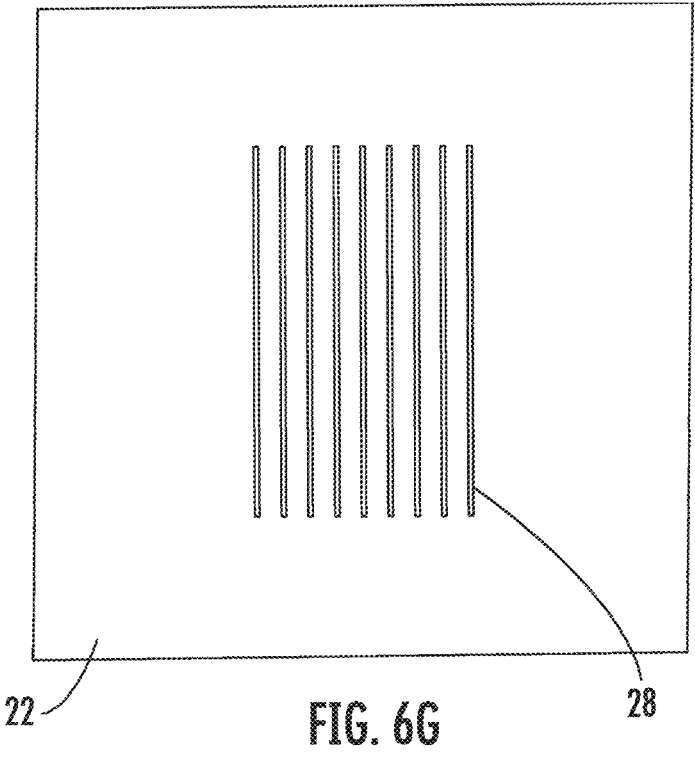

FIGS. 6A-6G illustrate views of a blade base, according to an embodiment of the present invention. As illustrated in FIGS. 6A-6G, the blade base 22 includes a number of slits 28. There is a corresponding slit 28 for each of the blades of the blade assembly. The blade base 22 can be formed from plastic, rubber, metal, or other material known to or conceivable to one of skill in the art. In some embodiments, all or a portion of the blade base can be removable after the cartilage is diced, in order to scrape any residual cartilage from the blades. In some embodiments, the blade base can also include screw holes 30 to couple the blade base 22 to the housing. In other embodiments the blade base 22 can be attached using another means or method known to or conceivable to one of skill in the art, or can be formed as one piece with the housing. The slits 28 can have a width from 0.1 mm to 15 mm with a 1-15 mm space in between the slits 28. The slits 28 have a length in the range of 35 mm-50 mm. While ranges are described herein, the size of the blades and the corresponding size of the slits can be varied. In some embodiments the blades may be larger or smaller, requiring changes to the size of the blade base 22. FIG. 6B illustrates an exemplary slit width of 0.3 mm. FIG. 6C illustrates a different embodiment with a 0.6 mm slit width. FIG. 6D illustrates an exemplary slit width of 1.5675 mm. FIGS. 6E, 6F, and 6G illustrate an exemplary slit length of 46 mm with each of the exemplary slit widths 1.5 mm, 0.6 mm, and 0.3 mm, respectively.

Figures 7A, 7B:
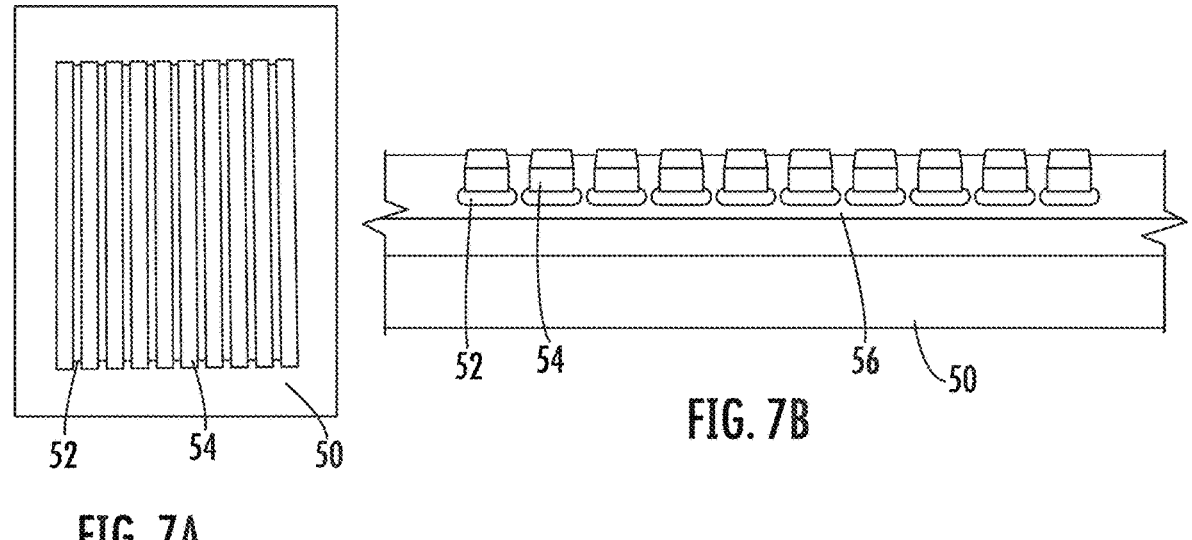
FIGS. 7A and 7B illustrate views of a columnar O-ring base with O-rings, according to an embodiment of the present invention.

FIGS. 7A and 7B illustrate views of a columnar O-ring base with O-rings, according to an embodiment of the present invention. The columnar O-ring base 50 and O-rings 52 illustrated in FIGS. 7A and 7B include columns 54 that extend alongside a length of a slit 56. As with the other embodiments, there are nine slits 56 illustrated for each of the nine blades of the blade assembly. In other embodiments, a different number of blades and consequently a different number of slits may be preferred. There is an O-ring 52 stretched around each of the columns 54, such that each blade has a portion of an O-ring 52 extending along each of its sides. In other words there are portions of two O-rings 52 extending along the sides of the blade. This further prevents cartilage from entering the housing. The O-rings can also be removed in order to collect more cartilage.

Figure 8A:
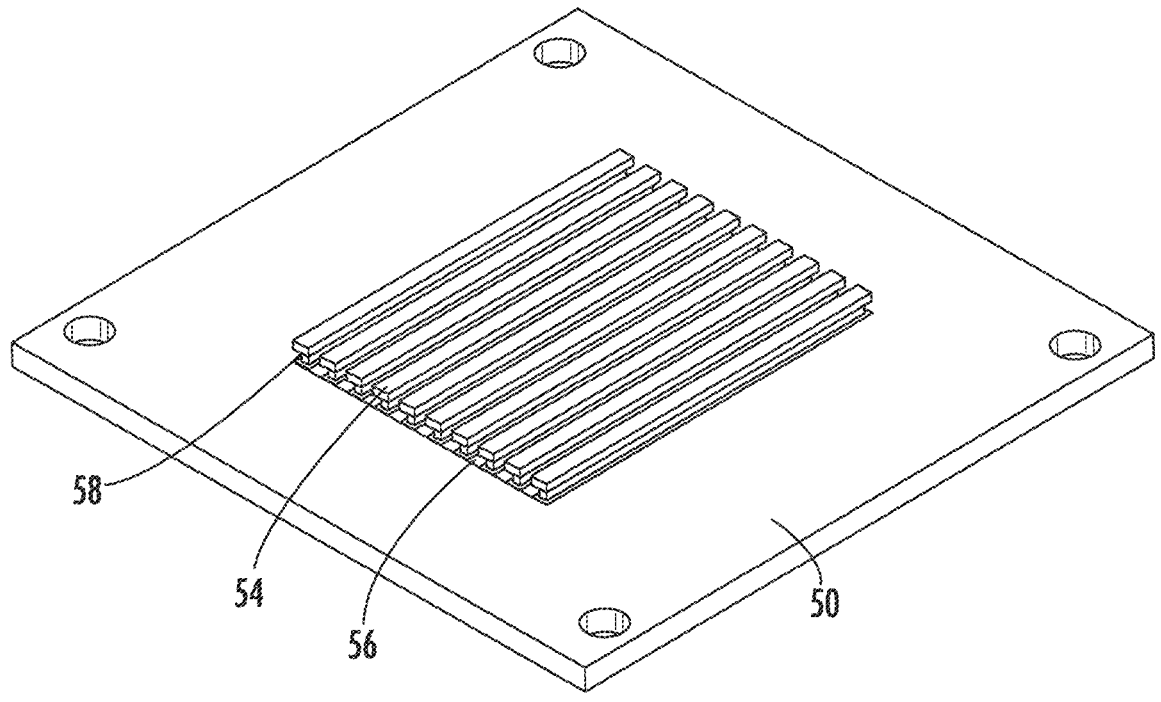
Figure 8B:
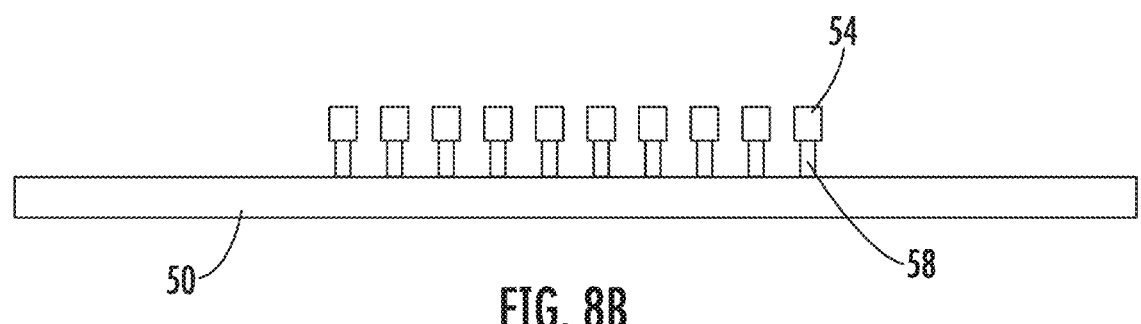
Figure 8C:
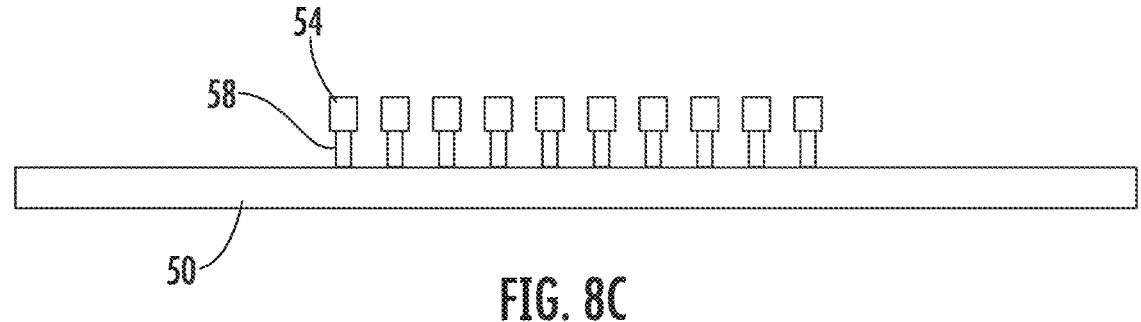
Figure 8D:
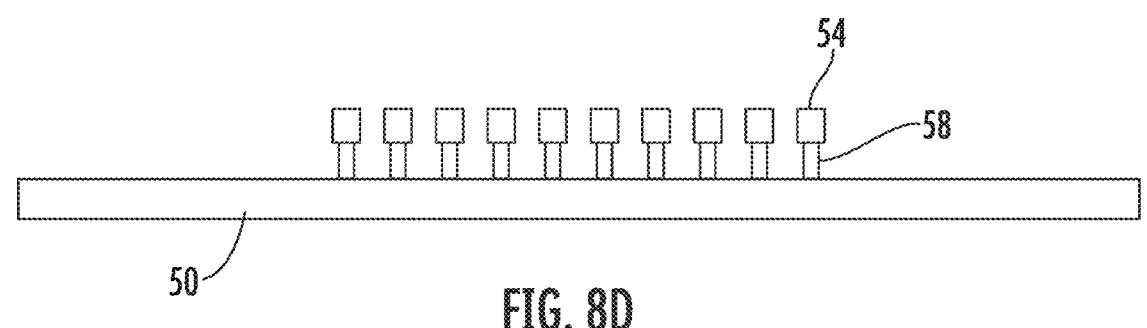
Figure 8E:
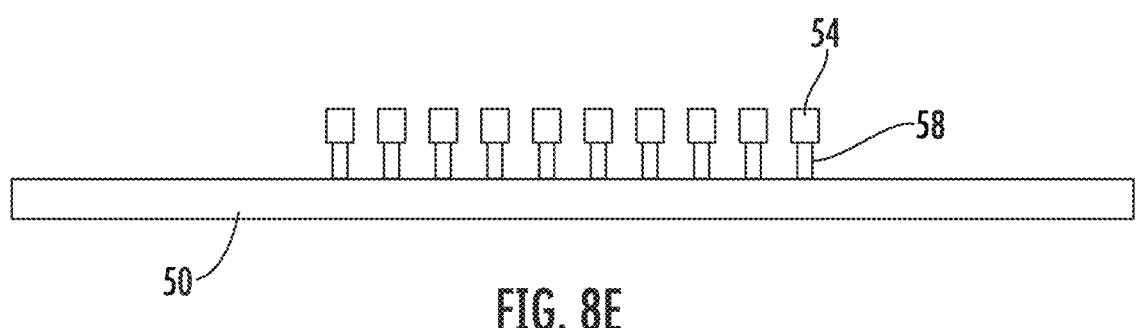
Figure 8G:
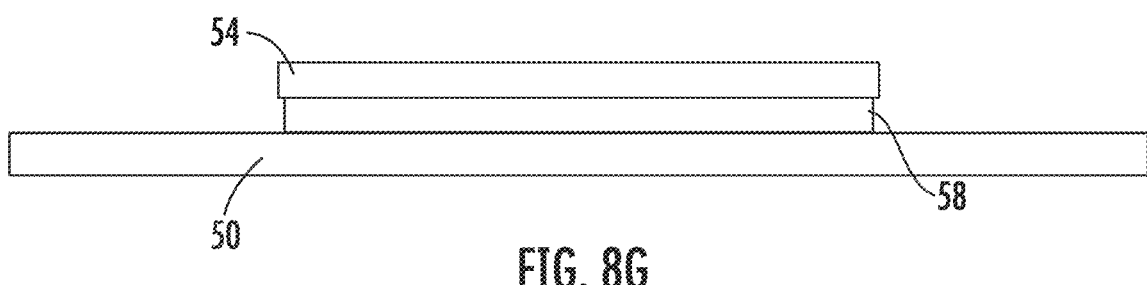

FIGS. 8A-8H illustrate views of a columnar O-ring base 50, according to an embodiment of the present invention. There are nine slits 56 illustrated for each of the nine blades of the blade assembly. In other embodiments a different number of blades and consequently a different number of slits may be preferred. O-ring columns 54 extend along each side of each of the slits 56. The O-ring columns 54 include grooves 58 to prevent the O-rings from moving longitudinally. There are ten O-ring columns 54 overall, such that there is a column on each side of the nine slits 56. As illustrated in FIG. 8B, the width of the base of the O-ring column is approximately 1 mm, in an exemplary embodiment. The width of the top of the O-ring column is 2 mm, in the exemplary embodiment illustrated in FIG. 8C. This difference in width creates the groove 58 to prevent the O-rings from moving longitudinally. FIG. 8D illustrates that the height of the top portion of the O-ring column is 2.5 mm in an exemplary embodiment, and FIG. 8E illustrates that the height of the top portion of the O-ring column is also 2.5 mm in an exemplary embodiment. The length of the top portion of the O-ring column is illustrated as 46 mm in the exemplary embodiment of FIG. 8E, and the length of the bottom portion of the O-ring column is illustrated as 45 mm in FIG. 8F.

Figure 9:
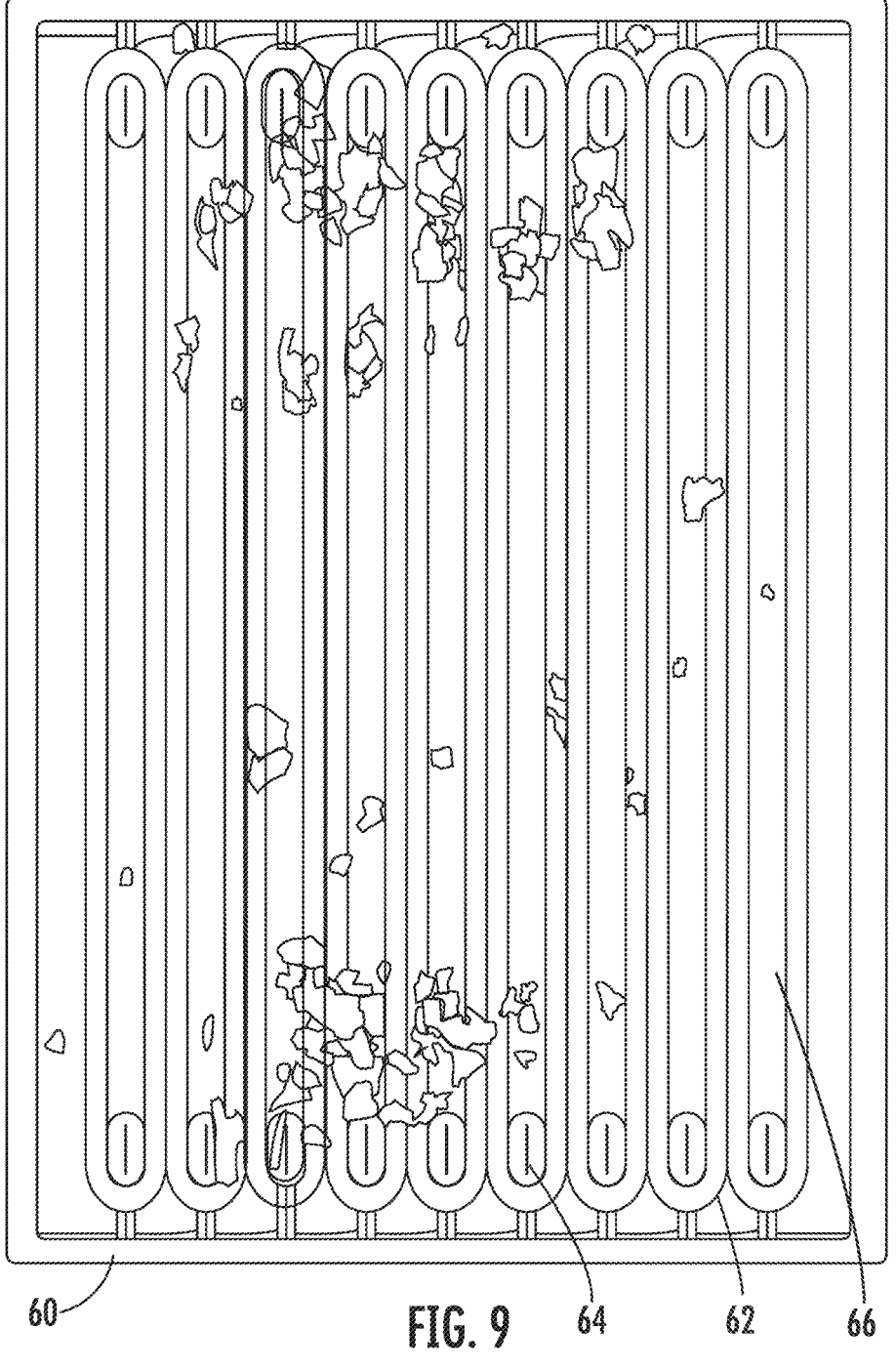
FIG. 9 illustrates a top-down view of a hooked O-ring base with O-rings, according to an embodiment of the present invention.
Figure 10A:
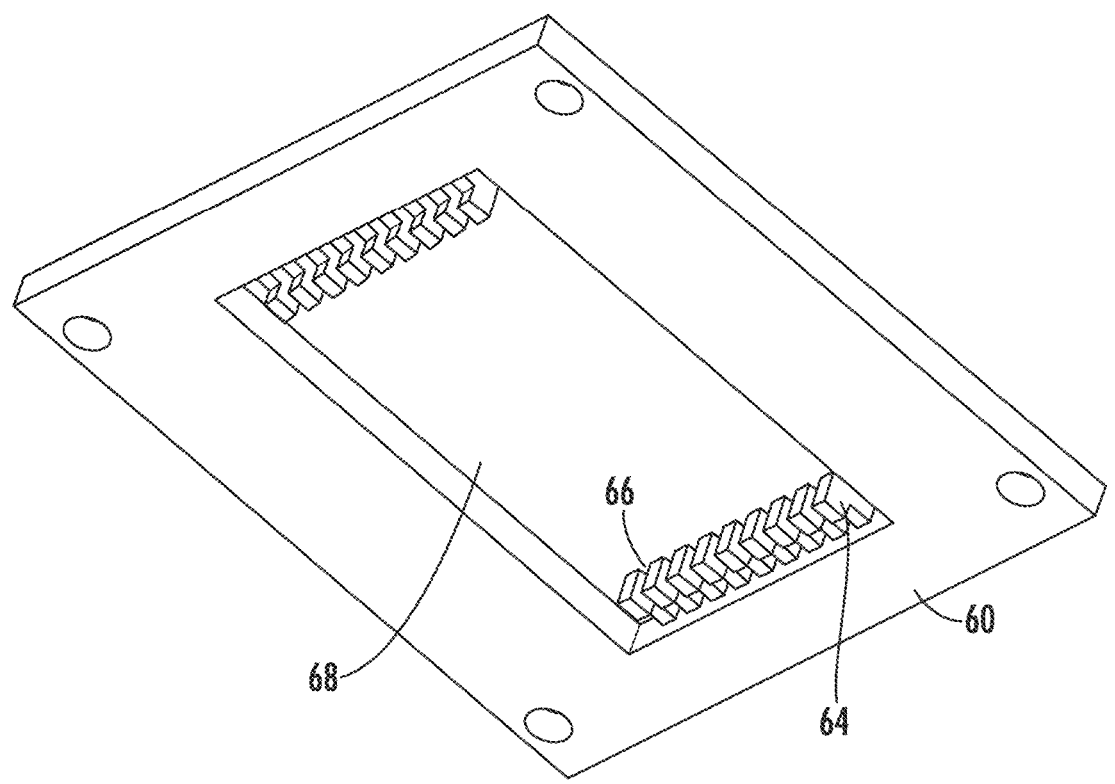
FIGS. 10A-10G illustrate views of a hooked O-ring base, according to an embodiment of the present invention.
Figure 10B:
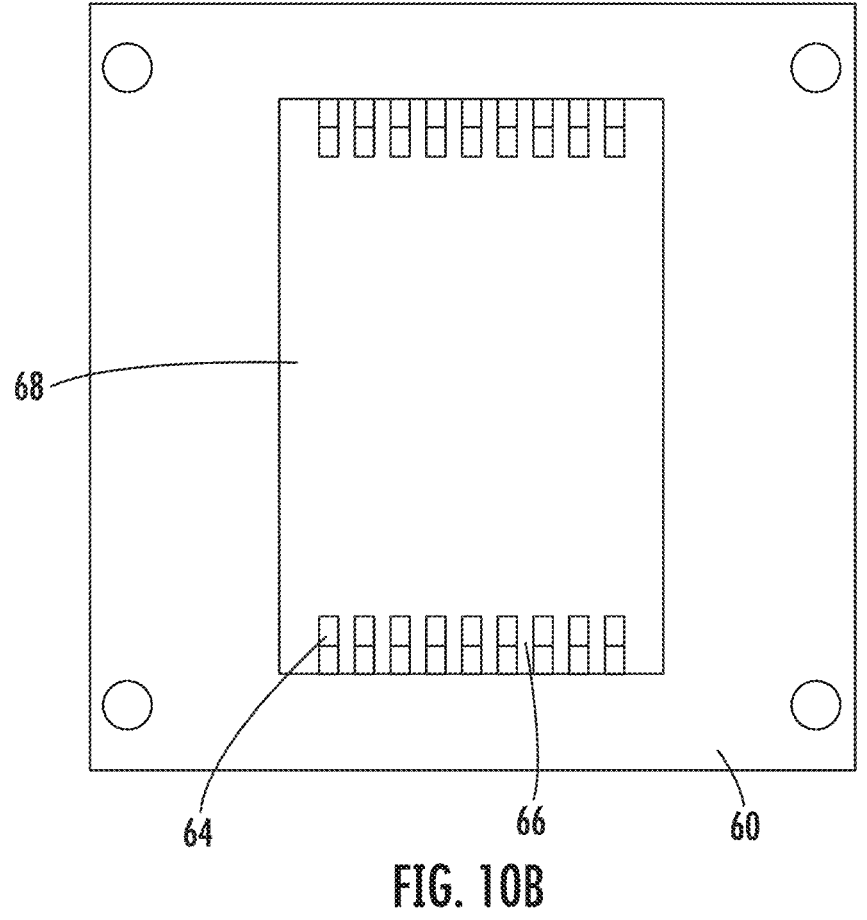
Figure 10C:
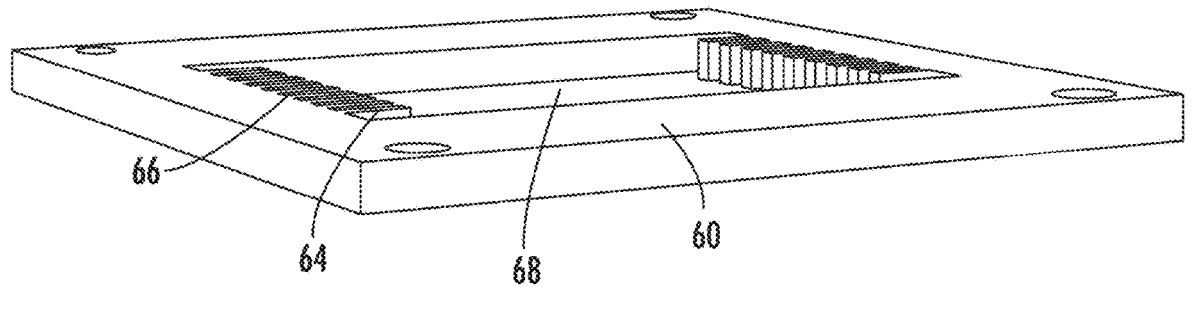
Figure 10D:
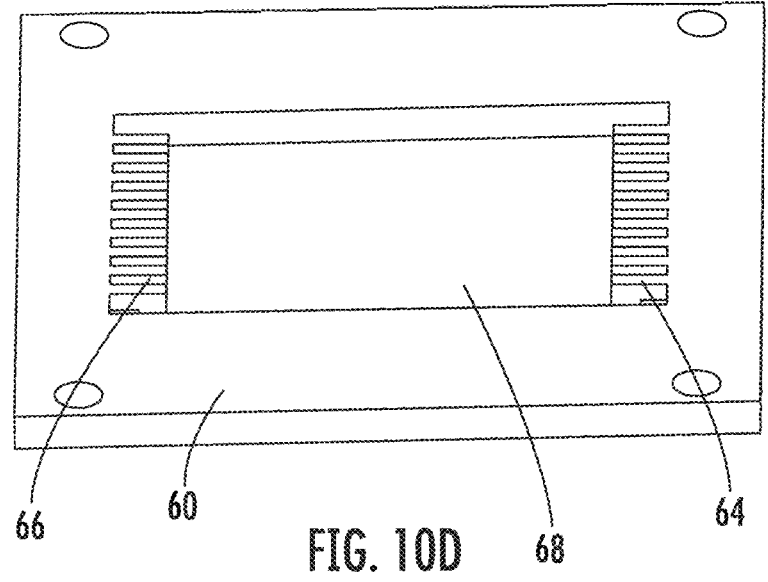
Figure 10E:
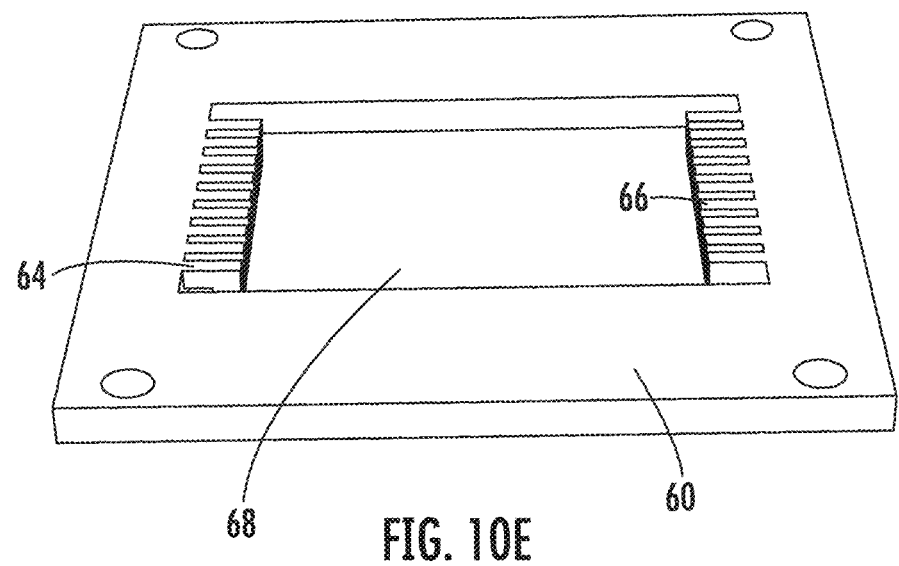
Figure 10F:
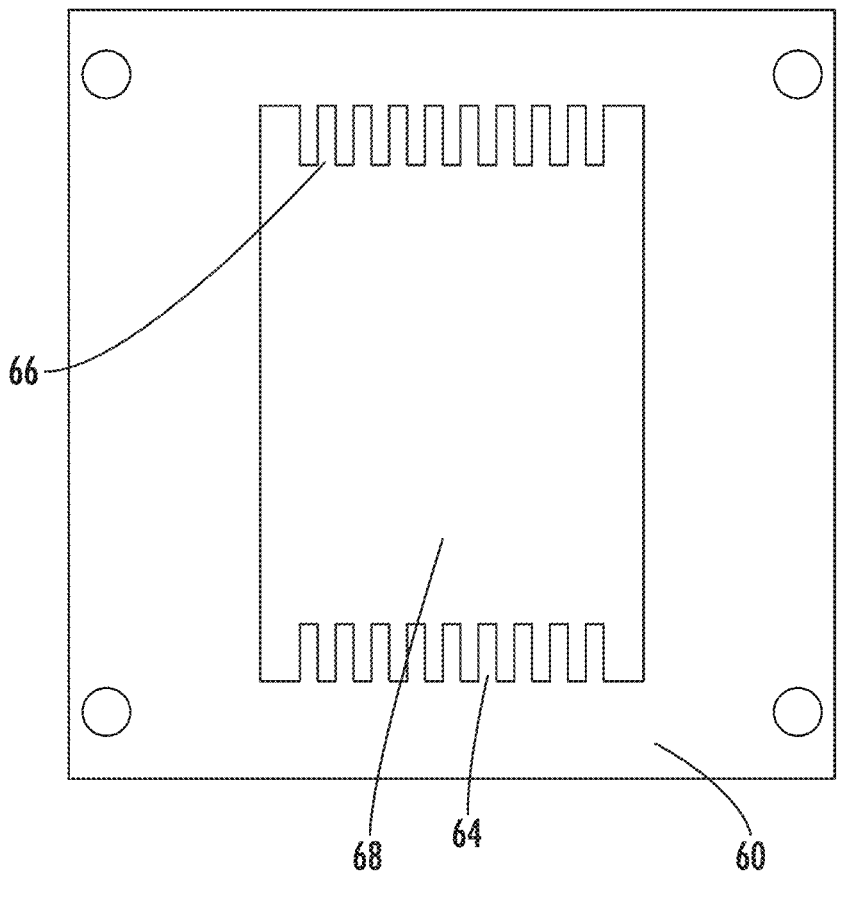
Figure 10G:
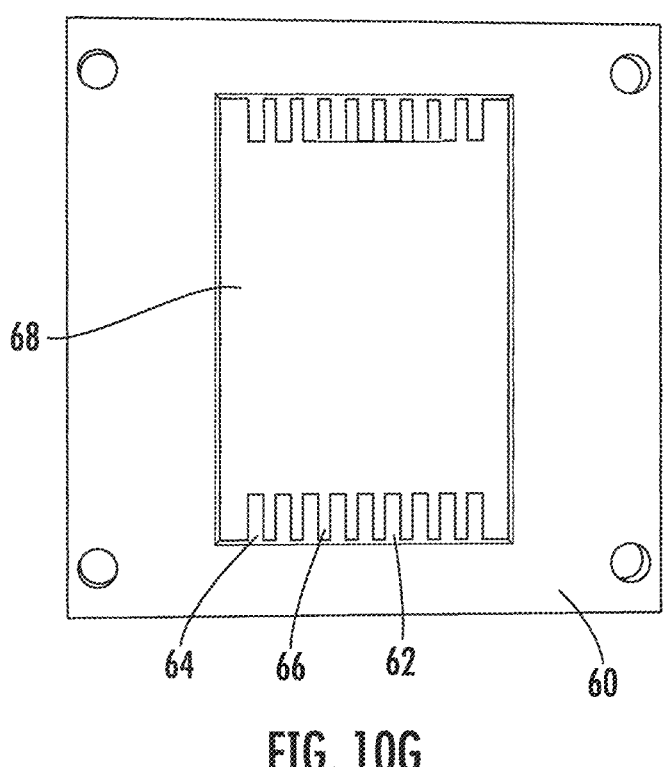

FIG. 9 illustrates a top-down view of a hooked O-ring base 60 with O-rings 62, according to an embodiment of the present invention. The O-ring hooks 64 and O-rings 62 illustrated in FIG. 9 includes hooks 60 that sit at each end of a slit 66. As with the other embodiments, there are nine slits 66 illustrated for each of the nine blades of the blade assembly. In other embodiments a different number of blades and consequently a different number of slits may be preferred. There is an O-ring 62 stretched between the hooks 64 positioned at each end of each of the slits 66, such that each blade has an O-ring 62 extending around it. This configuration further prevents cartilage from entering the housing. The O-rings can also be removed in order to collect more cartilage.

FIGS. 10A-10G illustrate views of a hooked O-ring base, according to an embodiment of the present invention. There are nine slits 66 illustrated for each of the nine blades of the blade assembly. In other embodiments, a different number of blades and consequently a different number of slits may be preferred. O-ring hooks 64 are positioned at each end of each of the slits 66. The O-ring base also defines an opening 68. There are 18 O-ring hooks 64 overall, such that there is one hook 64 positioned at each end of each of the slits 66. FIGS. 10B-10G illustrate exemplary dimensions of the hooked O-ring base 60. The height of the hooks is 4 mm, the length of the hooks is 6 mm. The length of opening 68 is 60 mm in an exemplary embodiment and the distance between hooks is 1.7 mm. The width of opening 68 is 40 mm in the exemplary embodiment. Any embodiment of the blade base described herein can be treated with a sealant in order to further reduce the space surrounding the blades of the blade assembly for preventing entry of tissue into the device.

Figure 11A:
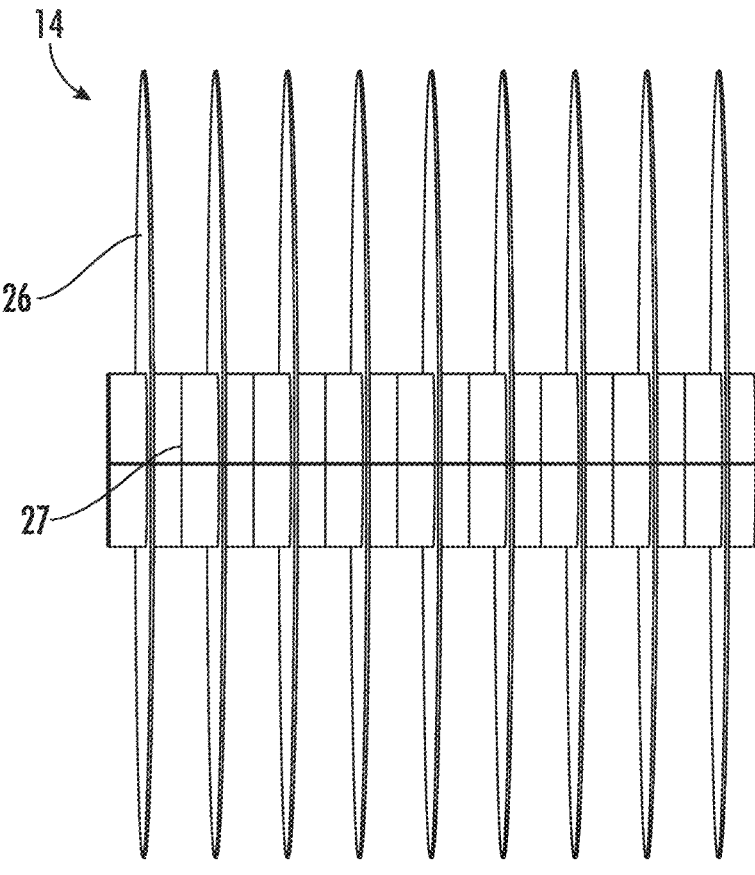
FIGS. 11A and 11B illustrate views of a blade assembly, according to an embodiment of the present invention.
Figure 11B:
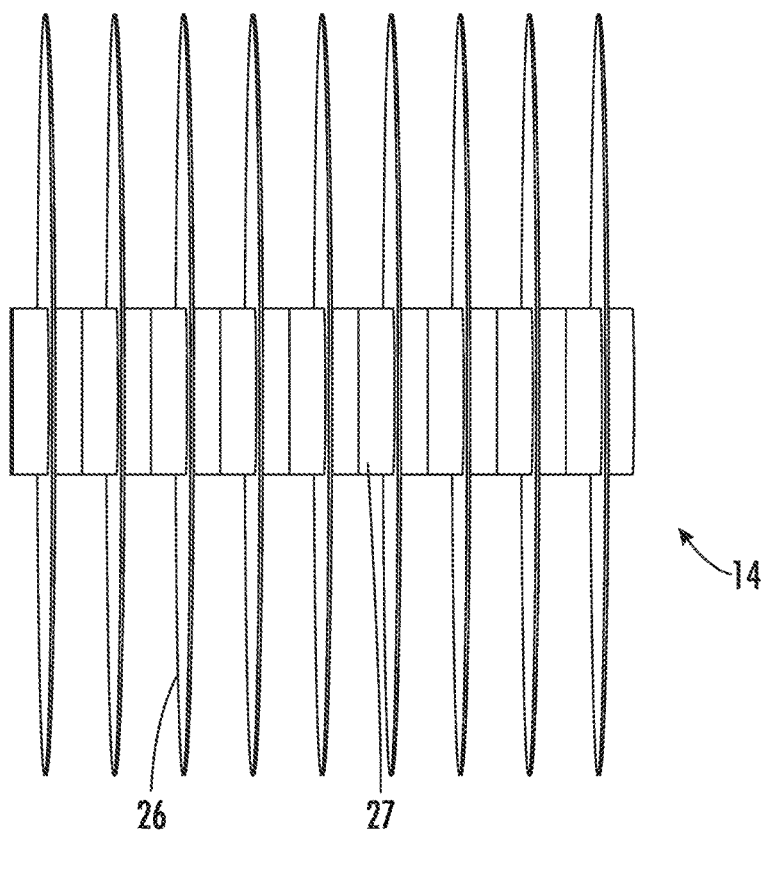
Figure 12:
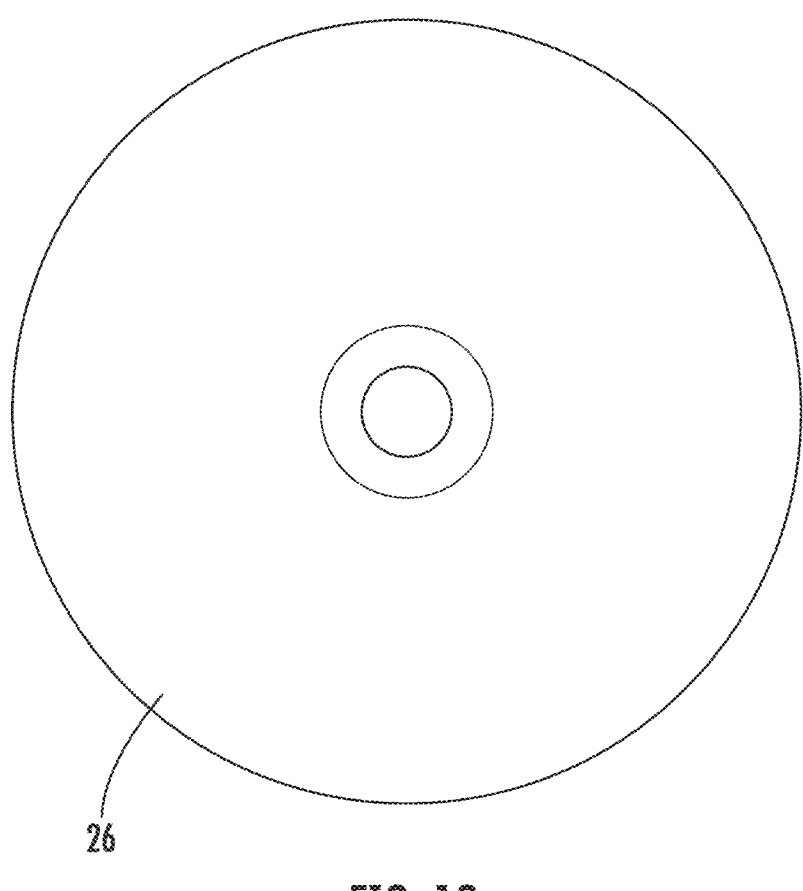
FIG. 12 illustrates a side view of a blade of the blade assembly, according to an embodiment of the present invention.

FIGS. 11A and 11B illustrate views of a blade assembly and FIG. 12 illustrates a side view of a blade, according to an embodiment of the present invention. The blade assembly 14 includes nine blades 26 separated by spacers 27. The spacers 27 are positioned between blades 26 and around an axle (not pictured). The blades 26 can be formed from a metal, ceramic, composite, or other material known to or conceivable to one of skill in the art. Each blade can be coated with a non-stick material, such as Teflon®. Alternately, a lubricating spray can be applied to prevent sticking. The blades may have a smooth sharpened edge. In other embodiments the blades may have serrated edges, varying radii, varying curvature, or any other blade design known to or conceivable to one of skill in the art.

As illustrated in FIGS. 11A and 11B, the blades have a 45 mm diameter and define a 5 mm opening in the center through which the axle is positioned. The spacers 27 can be removable and replaceable. In some embodiments, the spacers 27 can be replaced with spacers of different sizes to change the blade spacing. Blades can also be removable to further change and customize the blade spacing. In some embodiments, a mechanism can be included to vary the blade spacing on the fly. In some embodiments, the blade assembly can be used on its own without a housing. In such embodiments, the axle can further include a handle attached to axle ends for rolling the blade assembly back and forth over the tissue to be diced. While the blade assembly is described herein as rotating around a horizontal axis, in some embodiments the blades may be positioned about a vertical axle. In such an embodiment, the device will function more closely to a mixer, blender, or grinder. The blade assembly can also include gearing to increase the cutting force. The blade assembly can include a lock and fit assembly, such that the blade assembly can be ejected and replaced. The replacement assembly would also be configured to lock into place. In some embodiments, the blade assembly may be retractable into the housing. This would allow for further scraping of tissue from the blades and also allow the blades to be moved up and out of the way when the device is not in use. A slot and groove assembly could be used to retract the blades. In other embodiments the blade assembly could be biased downward with a spring-based mechanism, and retracted and locked into the housing. Any other suitable mechanism for retracting the blades known to or conceivable to one of skill in the art could also be used.

Figure 13:
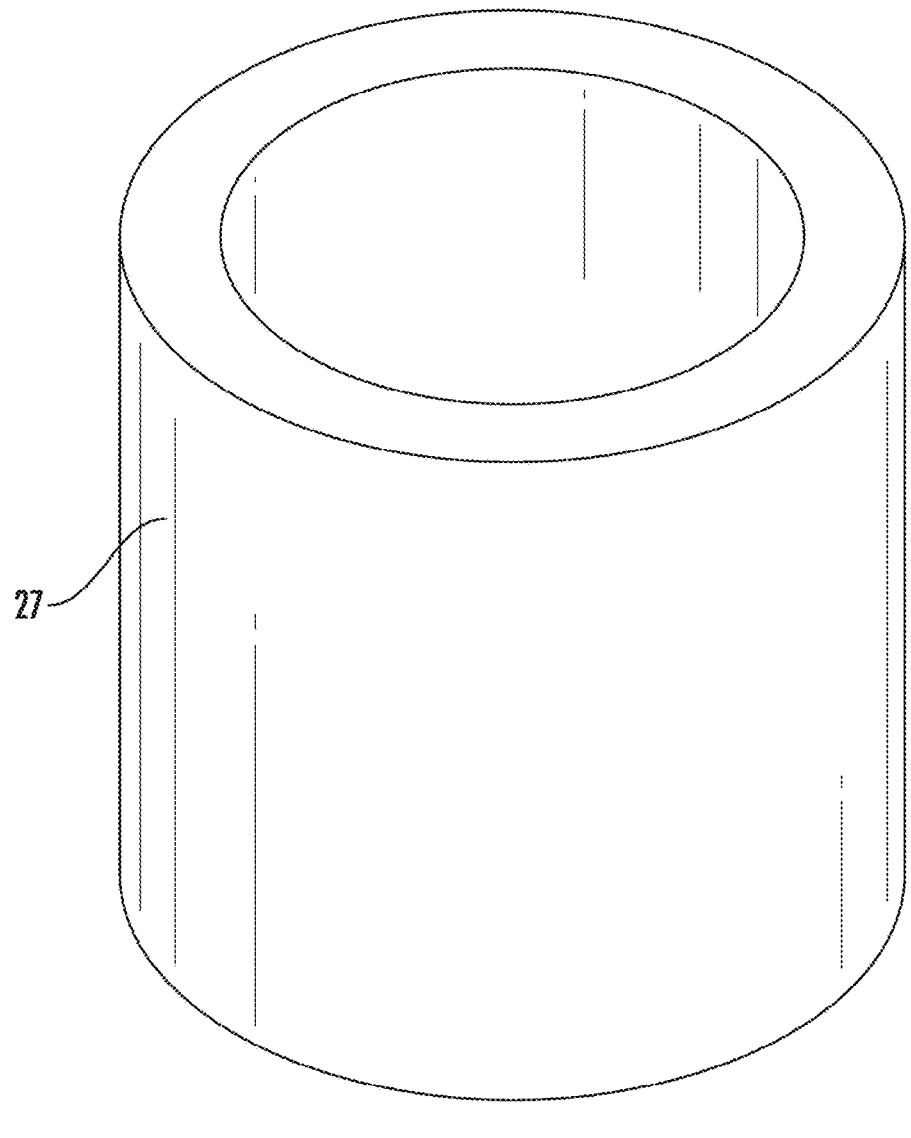
FIG. 13 illustrates a perspective view of a spacer, according to an embodiment of the present invention.

FIG. 13 illustrates a perspective view of a spacer, according to an embodiment of the present invention. The spacer 27 is cylindrical in shape and is configured to be positioned over the axle and between the blades. The spacer can be formed from a metal, plastic, or other material known to or conceivable to one of skill in the art.

Various configurations of a device according to the present invention were tested. These exemplary embodiments are included by way of example to further illustrate the invention and are not meant to be considered limiting. Some of these exemplary embodiments, include nine rotary blades (45 mm diameter, 0.3 mm width) arranged in parallel. These blades are pressure fit with plastic spacers on a metal axle. The blades are inserted through a base with nine 46 mm slits spaced at 4 mm apart. Each slit is 1.2 mm wide. The blades protrude through the bottom of the casing by approximately 15 mm. A box-like acrylic casing is positioned around the blades to provide a degree of ergonomic usability for testing. The device functioned by gripping the casing and rolling the device back and forth over cartilage on a flat surface. To mitigate the entry of cartilage into the device, four separate approaches were identified: decreased slit width (0.6 mm, 0.7 mm, 0.8 mm) of the bottom casing, decreased slit length of the bottom casing, the addition of a rubber membrane with blade slits on the bottom casing, and the use of two separate O-Ring mechanisms in the bottom of the casing. In some embodiments, components can be 3D printed.

Another design tested reduced the slit length to 40 mm. In another prototype, the impact on cartilage loss from adding a rubber membrane on the external side of the base was assessed. In contrast to simply reducing the width of the slits, which is limited by manufacturing constraints, it was hypothesized that the space in which diced cartilage can pass into the device could be minimized while maintaining the smooth rotation of the blades using a rubber membrane, which is more elastic than the plastic material comprising the base. A $\frac{1}{16}$" rubber base with a 70 A durometer was fitted to the size of the original base and razor blades were used to create extremely thin cuts aligned with the positions of the blades on the axle.

Two O-Ring iterations were also developed. The first includes two hooks at opposing ends of each blade slit, with an O-ring tensioned by the hooks around each blade. A second design increases the height of the material between the blade slits in the base and adds grooves along the "columns" for O-rings, so that a single blade would be flanked by two O-rings instead of surrounded by a single ring. In some embodiments the base is removable to scrape any remaining tissue off of the blades.

In some embodiments of the present invention, the device may include a cutting surface or work space divider to keep tissue from being lost to the environment while the device is being used. Alternately, the device can include an extended housing that extends from the housing to the cutting surface to further trap tissue and keep it from being lost to the environment. In some embodiments, this extended housing can be formed from a clear material in order to preserve visualization of the cutting process. Having a dedicated workspace, cutting surface or extended housing can also prevent contamination of the tissue.

While the device is described with respect to the example of dicing of cartilage for rhinoplasty or other plastic surgery, it can be used for any number of applications where the goal is to dice matter with minimal loss of that matter within the dicing mechanism. Additional medical and surgical applications, include but are not limited to, scaffolds and structural grafts. Scaffolding examples, include but are not limited to, arthroscopic tissue scaffolding for knee repair, regeneration of cartilage and subchondral bone interface, and articular cartilage injury. Examples of structural grafts, include but are not limited to, structural grafting in rhinoplasty, three-dimensional columellar strut grafts, and concentric and eccentric carved costal cartilage. A device according to an embodiment of the present invention can be used for dicing tissue for autopsy or histological applications. The use can be for humans, animals, insects, in vitro tissue or samples, or any other source of sample material known to or conceivable by one of skill in the art. In addition, a device according to the present invention can be used for industrial applications, including but not limited to food processing, such as industrial processing of vegetables and meat. A device according to the present invention could also be used as a consumer-facing food processing tool. A device according to an embodiment of the present invention can also be used for pre-processing of tissue by tissue banks. A number of exemplary uses are contemplated herein. It should be noted that these examples are not meant to be considered limiting. A device according to an embodiment of the present invention could be used for any application known to or conceivable to one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device assembly comprising:
a blade base;
a housing comprising a portion, extending vertically from a top surface of the blade base, that is a handle for a user to move the device assembly; and
a blade assembly configured to cut tissue,
wherein the blade base comprises one or more O-rings, configured to scrape tissue from the blade assembly, and one or more anchors configured to hold the one or more O-rings in place.

2. The device assembly of claim 1,
wherein the blade assembly comprises a blade.

3. The device assembly of claim 2,
wherein the blade is a circular blade.

4. The device assembly of claim 2,
wherein the blade is configured to rotate about an axis.

5. The device assembly of claim 1,
wherein the blade assembly comprises a plurality of blades.

6. The device assembly of claim 1,
wherein the blade base comprises a slit to accommodate the blade assembly.

7. The device assembly of claim 1,
wherein the one or more anchors comprise hooks.

8. The device assembly of claim 1,
wherein the one or more anchors comprise columns.

9. The device assembly of claim 1,
wherein the blade base comprises a removable portion configured to scrape tissue from the blade assembly.

10. A device assembly, comprising:
a blade base;
a housing comprising a portion, extending vertically from a top surface of the blade base, that is a handle for a user to move the device assembly; and
a blade assembly configured to cut tissue,
wherein the blade base comprises:
one or more O-rings configured to scrape tissue from the blade assembly,
an opening configured to accommodate the blade assembly, and
a material, surrounding the opening, configured to further remove tissue from the blade assembly.

11. The device assembly of claim 10,
wherein the blade assembly comprises a blade.

12. The device assembly of claim 11,
wherein the blade is a circular blade.

13. The device assembly of claim 11,
wherein the blade is configured to rotate about an axis.

14. The device assembly of claim 10,
wherein the blade assembly comprises a plurality of blades.

15. The device assembly of claim 10,
wherein the blade base comprises a removable portion configured to scrape tissue from the blade assembly.

16. The device assembly of claim 10,
wherein the housing is configured to protect a hand of the user from the blade assembly.

17. The device assembly of claim 10,
wherein the blade assembly is retractable into the housing.

18. A device, comprising:
a blade base;
a housing comprising a portion, extending vertically from a top surface of the blade base, that is a handle for a user to move the device; and
a blade assembly, in the blade base and the housing, comprising one or more O-rings configured to scrape tissue from the blade assembly,
wherein the housing is removable from the blade base to access the blade assembly.

19. The device of claim 18,
wherein the blade assembly comprises a circular blade.

20. The device of claim 19,
wherein the circular blade is configured to rotate about an axis.

* * * * *